United States Patent [19]

Ong et al.

[11] Patent Number: 4,766,255

[45] Date of Patent: Aug. 23, 1988

[54] PROCESSES FOR BISPHENOLS

[75] Inventors: Beng S. Ong, Mississauga; Lupu Alexandru, Toronto, both of Canada

[73] Assignee: Xerox Corporation, Stamford, Conn.

[21] Appl. No.: 67,588

[22] Filed: Jun. 29, 1987

[51] Int. Cl.$^4$ .............................................. C07C 39/16
[52] U.S. Cl. .................................... 568/728; 568/727
[58] Field of Search ................................ 568/727, 728

[56] References Cited

U.S. PATENT DOCUMENTS

| | | | |
|---|---|---|---|
| 1,760,758 | 5/1930 | Korten | 568/715 |
| 2,069,560 | 2/1937 | Rothrock | 260/154 |
| 2,069,573 | 2/1937 | Bolton | 260/154 |
| 2,858,342 | 10/1958 | Bender et al. | 260/619 |
| 4,053,522 | 10/1977 | McGlure et al. | 568/728 |
| 4,169,211 | 9/1979 | Ligorati et al. | 568/728 |
| 4,375,567 | 3/1983 | Faler | 568/728 |
| 4,423,252 | 12/1983 | Maki et al. | 568/728 |
| 4,590,303 | 5/1986 | Mandiratta | 568/728 |

*Primary Examiner*—Werren B. Lone
*Attorney, Agent, or Firm*—E. O. Palazzo

[57] ABSTRACT

A process for the preparation of gem-bis(hydroxyaryl)alkanes which comprises the reaction of a ketone, a hydroxyarene and an alkylhalosilane.

27 Claims, No Drawings

PROCESSES FOR BISPHENOLS

BACKGROUND OF THE INVENTION

This invention is generally directed to processes for the preparation of bisphenols such as gem-bis(hydroxyalkyl)alkanes, and more specifically to processes for preparing 1,1-bis(p-hydroxyphenyl)cyclohexane, commonly referred to as bisphenol (Z). Thus, in accordance with the process of the present invention there can be prepared certain bisphenols, inclusive of bisphenol (Z) by the reaction of a ketone, a hydroxyarene such as a phenol, and an alkylhalosilane, which functions as a condensation mediating component. There is thus enabled with the process of the present invention a simple economical method for the synthesis in high yields of bisphenols, which can be selected as a monomer for the preparation of polycarbonates that are useful as binders for charge transport molecules, and photogenerating pigments incorporated, for example, into layered photoconductive imaging members, reference U.S. Pat. No. 4,265,990, the disclosure of which is totally incorporated herein by reference. In one important embodiment of the present invention, there is provided a process for the preparation of specific bisphenols by the reaction of a ketone, a phenol and an alkylhalosilane mediating agent in the presence of a catalyst, wherein there results products in yields of, for example, greater than 65 percent, which products are substantially free of undesirable impurities. The aforementioned bisphenols, particularly bisphenol (Z) as indicated herein, can be selected for the preparation of polycarbonate resins, which resins can be utilized as binder components in layered imaging members. More specifically, the polycarbonates obtained can be selected as resinous binders for arylamines, inclusive of triarylamine charge transport components.

Processes for the preparation of bisphenols are known, and generally involve the condensation of two mole equivalents of phenol with one mole equivalent of carbonyl compound in the presence of an acid catalyst. Acid catalysts employed for the aforementioned condensation are concentrated hydrochloric acid, gaseous hydrogen chloride, concentrated sulfuric acid, hydrogen fluoride, hydrogen bromide, boron trifluoride, boric acid, ferric chloride, phosphorus chloride, phosphorus pentoxide, benzenesulfonic acid, and the like. Although these acid catalysts, in particular gaseous hydrogen chloride, are very effective in promoting the condensation of phenols with sterically accessible ketones such as acetone, they are not effective for the preparation of bisphenols, especially bisphenol (Z) derived from the sterically demanding small cyclic ketone such as cyclopentanone or cyclohexanone. The condensation with small ring ketones does not normally proceed in a rapid manner, and the yield of product is generally less than desirable. The aforementioned reaction, especially when accomplished in the presence of hydrogen chloride as a catalyst, is illustrated in U.S. Pat. No. 4,304,899. Similar teachings are presented in U.S. Pat. Nos. 1,760,758; 2,069,560 and 2,069,573, wherein there are disclosed methods for the preparation of bisphenols with hydrogen chloride catalysts.

In U.S. Pat. No. 2,858,342, there is disclosed, for example, a method for the preparation of bisphenols utilizing alkali metal phenoxides, or alkaline earth metal phenoxides of the phenol being reacted; and wherein cyclohexanone may be selected as a reactant. There resulted in one process embodiment illustrated in this patent, reference Example XI, the preparation of 1,1-bis-(4-hydroxyphenyl)cyclohexane. Also, there is described in U.S. Pat. No. 4,423,352 a process for the preparation of bisphenols utilizing a cation exchange resin modified with a pyridine alkanethiol as a catalyst.

Moreover, U.S. Pat. No. 1,977,627 describes a process for the preparation of bisphenols wherein 65 to 75 percent sulfuric acid is selected as the catalyst. With the process as disclosed in the '627 patent, there is avoided a complex apparatus, and moreover corrosion problems are substantially reduced. In comparison to the processes mentioned herein, wherein, for example, hydrogen chloride is selected as a catalyst, the process of the '627 patent proceeds in a less rapid manner and the product resulting is more difficult to purify. Additionally, it is known that certain sulfur compounds such as sulfur dichloride, sodium thiosulfate, sodium sulfide and the like can be selected for the synthesis of bisphenols, reference for example U.S. Pat. No. 2,923,744, which illustrates a process for the preparation of bisphenols wherein there is selected mercaptoalkanesulfonic acids in catalytic amounts for the purpose of promoting the condensation of phenols and carbonyl compounds. Similarly, selenium and tellurium compounds are effective catalysts for bisphenol synthesis, reference for example U.S. Pat. No. 2,762,846.

Accordingly, while processes for the preparation of bisphenols are known, there is a need for new processes particularly those wherein products with acceptable yields are obtained. More specifically, there is a need for processes for the preparation of bisphenols that are economical, and where there are provided excellent yields of the product desired. There is also a need for efficient, simple processes for the preparation of bisphenols. Additionally, there is a need for processes for the synthesis of bisphenols wherein the products resulting are substantially free of impurities, enabling their use, for example, in the preparation of polycarbonates that can be selected as binders in electrophotographic imaging members. In addition, there is a need for economical processes that enable the preparation of bisphenols where the reaction can be rapidly accomplished at a relatively low temperature. Another need resides in the provision of a simple efficient process wherein the bisphenol product resulting can be easily purified such as by simple recrystallization, and the excess of reagent selected can be recovered by filtration. Also, there is a need for efficient processes that permit the preparation of certain bisphenols wherein troublesome gaseous catalysts are avoided.

SUMMARY OF THE INVENTION

It is therefore an object of the present invention to provide processes for the preparation of bisphenols.

A further object of the present invention is the provision of an economical process for the preparation of bisphenols.

Additionally, in a further object of the present invention there are provided processes for the preparation of bisphenols with acceptable yields.

Another object of the present invention resides in the preparation of bisphenol (Z) in excellent yields by the reaction of cyclohexanone and phenol in the presence of a alkylhalosilane, which processes can be rapidly accomplished at relatively low temperatures.

In yet another specific object of the present invention there are provided processes for the preparation of certain bisphenols which are substantially free of impurities.

Furthermore, in yet another object of the present invention there are provided processes for the preparation of specific bisphenols in yields of at least 65 percent, and wherein the resulting products can be selected for the preparation of polycarbonates that are useful as binders for charge transport molecules, and for photogenerating pigments in layered photoconductive imaging members.

Also, in another object of the present invention there are provided efficient, simple processes for the preparation of purified bisphenol (Z) in excellent yields of from about 65 to about 95 percent, for example.

A further object of the present invention is to provide an operationally simple process wherein the product bisphenol can be purified by simple washing with, or by recrystallization from suitable solvents.

Additionally, a further object of the present invention is to provide an efficient process wherein chlorotrimethyl silane and a thiol are utilized to affect a rapid condensation between phenols and ketones enabling the corresponding bisphenol products.

These and other objects of the present invention are accomplished by a process for the preparation of bisphenols that comprises the condensation of a hydroxyarene such as a phenol and a ketone in the presence of a alkylhalosilane. More specifically, the present invention is directed to the preparation of bisphenols, which comprises the reaction of ketones and phenols in the presence of halotrialkylsilanes and a thiol catalyst. In one specific embodiment of the present invention, bisphenols are obtained by reacting ketones with an excess of phenols in the presence of a stoichiometric quantity of chlorotrimethyl silane and a catalytic amount of, for example, an alkanethiol.

Accordingly, in one embodiment of the present invention there is prepared bisphenol (Z) by the reaction of cyclohexanone, and an excess amount of phenol in the presence of a stoichiometric quantity of chlorotrimethyl silane and a catalytic amount of butanethiol, which reaction is accomplished at a temperature of from about 30° to 65° C. and is illustrated with reference to the following illustrative reaction scheme.

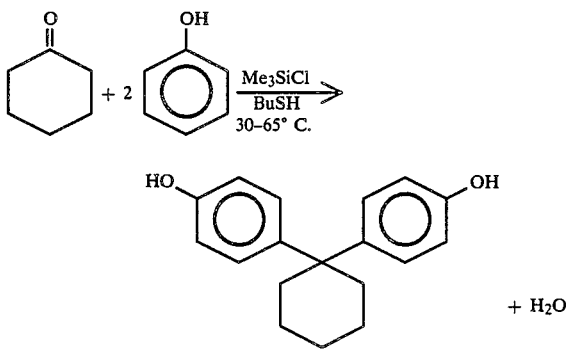

Illustrative examples of ketones usually selected in one mole equivalent that may be utilized for the process of the present invention include acetone, butanones, pentanones, cyclopentanone, substituted cyclopentanones, cyclohexanone, substituted cyclohexanones, and the like.

As hydroxyarenes, such as phenol, present in an amount of from about 2 to 10 mole equivalents, there can be selected for the process of the present invention phenol, cresols, ethylphenols, halophenols, cyanophenols, nitrophenols, naphthols, and the like.

Examples of alkylhalosilanes, present in an amount of from about 0.1 to 3 mole equivalents that can be selected for the process of the present invention include chlorotrimethyl silane, dichlorodimethyl silane, methyltrichloro silane, bromotrimethyl silane, fluorotrimethyl silane, chlorotriethyl silane, bromotriethyl silane, fluorotriethyl silane, and other similar silanes wherein the alkyl substituent contains, for example, from 1 to about 10 carbon atoms; and the halogen substituent can be fluoro, chloro, bromo, or iodo.

Illustrative examples of optional catalysts present in an amount of from about 0.001 mole equivalent to about 0.05 mole equivalent that may be selected for the process of the present invention include alkyl, from about 1 to 20 carbon atoms, and aryl, from about 6 to about 24 carbon atoms, thiols such as ethanethiol, propanethiol, butanethiol, and benzenethiol, mercaptopropionic acid, and the like.

The aforementioned reaction can be effected in the presence of an optional solvent. Suitable solvent examples include halogenated hydrocarbons such as methylene chloride, dichloroethane, chlorobenzene and the like; toluene, nitromethane, and nitrobenzene, which solvents are usually present in an amount of from 1 to about 75 percent by volume of the total reaction mixture.

With further respect to the process of the present invention, generally the reactants are mixed together in an appropriate reaction vessel and heated at a temperature of from about 30° to about 80° C., and preferably at a temperature of from about 30° to about 65° C.

Examples of bisphenols obtained in accordance with the process of the present invention include bisphenol (Z), bisphenol A, 1,1-bis(p-hydroxyphenyl)cyclopentane, 3,3-bis(p-hydroxyphenyl)pentane, 2,2-bis(p-hydroxyphenyl)pentane, 2,2-bis(p-hydroxyphenyl)butane, 1,1-bis(3-methyl-4-hydroxyphenyl)cyclohexane, 2,2-bis(3-methyl-4-hydroxyphenyl)propane, 3,3-bis(3-methyl-4-hydroxyphenyl)pentane, and the like. These bisphenols are separated from the reaction mixture by simple filtration or distillation, and purified either by washing with suitable solvents or recrystallization. The aforementioned products are generally characterized by NMR spectroscopy, and by comparison with authenticated samples of these bisphenols.

The aforementioned bisphenol products can be selected for the preparation of known polycarbonates by the reaction thereof with carbonate precursors such as phosgene, diacyl halides, bishaloformates, diesters, and diarylcarbonates. Polycondensation of bisphenols with phosgene, diacyl halide and bishaloformate can be executed in a suitable medium such as methylene chloride in the presence of a base such as pyridine. Also, the polycondensation reaction can also be conveniently accomplished by interfacial polymerization. The polycondensation of a bisphenol with a diester or diarylcarbonate requires an efficient catalyst such as titanium alkoxides, high temperatures, and high vacuum with an efficient condenser to remove the displacement byproduct. More specifically, polycarbonates such as PC(A) and PC(Z), for instance, are respectively prepared by reacting at room temperature stoichiometric quantities of bisphenol A and bisphenol (Z) with phosgene in methylene chloride in the presence of pyridine. These polycarbonates can also be prepared by interfacial polymerization of bisphenols with phosgene in a water methylene chloride medium containing a suitable water soluble base. Further, the aforementioned polycarbonates can be synthesized by transesterification with diphenylcarbonates in the presence of a catalyst such as titanium isopropoxide at high temperatures under high vacuum conditions. In the latter process, an efficient stirring mechanism and a cooling system to remove the phenol byproduct during the course of the polymerization can be utilized.

Polycarbonates with a weight average molecular weight, Mw, of from about 15,000 to about 100,000 prepared from the bisphenols obtained in accordance with the process of the present invention are useful as resinous binders for photogenerating pigments and charge transport molecules in layered photoresponsive imaging members as illustrated, for example, in U.S. Pat. No. 4,265,990, the disclosure of which is totally incorporated herein by reference. More specifically, these members are usually comprised of a supporting substrate, a photogenerating layer containing therein from about 85 to about 99 percent by weight of trigonal selenium, metal phthalocyanines, or metal free phthalocyanines, dispersed in the polycarbonate resinous binder present in an amount of from about 1 to about 15 percent by weight; and a charge transport layer comprised of, for example, aryl amines of the formula as illustrated in the '990 patent, and copending application U.S. Ser. No. 851,051 relating to organic photoconductive imaging members, the disclosure of which is totally incorporated herein by reference. The aforementioned photoconductive imaging members can be incorporated into numerous imaging and printing processes and apparatuses inclusive of xerographic imaging methods.

Various suitable charge transport layers can be selected for the photoconductive imaging members illustrated herein, which layer has a thickness of from about 5 microns to about 50 microns; and preferably is of a thickness of from about 10 microns to about 40 microns. In a preferred embodiment, this transport layer comprises aryl amine molecules of the following formula

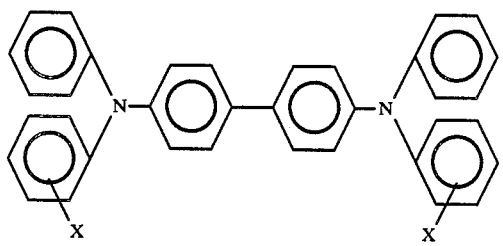

dispersed in a highly insulating and transparent polycarbonate resinous binder wherein X is selected from the group consisting of alkyl and halogen, such as (ortho)$CH_3$, (meta)$CH_3$, (para)$CH_3$, (ortho)Cl, (meta)Cl, and (para)Cl. The aforementioned polycarbonate binders can be prepared from the bisphenols synthesized in accordance with the process of the present invention.

Compounds corresponding to the above formula include, for example, N,N'-diphenyl-N,N'-bis(alkylphenyl)-[1,1-biphenyl]-4,4'-diamine wherein alkyl is selected from the group consisting of methyl, ethyl, propyl, butyl, hexyl and the like. With halo substitution, the amine is N,N'-diphenyl-N,N'-bis(halophenyl)-[1,1'-biphenyl]-4,4'-diamine wherein halo is 2-chloro, 3-chloro or 4-chloro.

With further respect to the products obtained from the process of the present invention, they can be selected as intermediates for the preparation of resins such as polyesters that are useful for incorporation into toner compositions, and moreover the bisphenols prepared have other known utilities including their use as pesticides.

The invention will now be described in detail with reference to specific preferred embodiments thereof, it being understood that these examples are intended to be illustrative only. Also, this invention is not intended to be limited to the materials, conditions, or process parameters recited herein.

EXAMPLE I

Preparation of 1,1-Bis(p-hydroxyphenyl)cyclohexane (Bisphenol Z) in the Presence of a Thiol Catalyst A mixture of 98.15 grams of cyclohexanone, 470 grams of phenol ($C_6H_5OH$), 1.0 gram of butanethiol, and 150 milliliters of 1,2-dichloroethane was charged into a 2-liter 3-necked round-bottomed flask fitted with a mechanical stirrer, a dropping funnel, and a reflux condenser. To the reaction flask was added 108 grams of chlorotrimethyl silane through the dropping funnel over a period of 5 minutes, and the resulting mixture was stirred, and heated in an oil bath at 50° to 55° C. under a nitrogen atmosphere. The colorless reaction mixture turned brown in color after 5 minutes of heating, and evolution of HCl gas was observed. Precipitation of the product from the reaction medium was noted after about 15 minutes. During this time, the temperature of the reaction mixture rose gradually, and reached a final temperature of 65° C. after 60 minutes. The stirring and heating were continued for another 1.5 hours before the oil bath was removed. After cooling to room temperature, the mixture was filtered by suction filtration, and the crude solid product obtained was slurried up in 500 milliliters of methylene chloride and filtered. The filtered product was further washed twice with methylene chloride. Recrystallization from a methanol and water mixture afforded 218 grams of the above pure bisphenol (Z) product with a melting point of 195° to 197° C. Also, High Performance Liquid Chromatography (HPLC) analysis indicated that the product had a purity of 99.2 percent.

EXAMPLE II

Preparation of Bisphenol (Z) Without a Thiol Catalyst

Bisphenol (Z) was also prepared by repeating the procedure of Example I with the exceptions that the reaction mixture was heated at 55° C. for 5 hours, and the butanethiol catalyst was not selected. The yield of bisphenol (Z) product was 75 percent.

EXAMPLE III

Preparation of 3,3-Bis(p-hydroxyphenyl)pentane 3,3-Bis(p-hydroxyphenyl)pentane was prepared by repeating the procedure of Example I with the exceptions that 86 grams of 3-pentanone, and 0.5 gram of propanethiol were respectively employed in place of the cyclohexanone and butanethiol. The purity of the resulting above product was 99.5, and it had a melting point of 207° to 208° C. NMR data for this product was as follows:

NMR(Acetone-d$_6$), δ(ppm): 0.6(t, 6H); 2.5(t, 4H); 6.65 to 7.10(AA'BB', 8H); 8.15(s, 2H).

EXAMPLE IV

Preparation of 2,2-Bis(p-hydroxyphenyl)propane (Bisphenol A)

Into a 250-millimiter 3-necked round-bottomed flask was charged a mixture of 11.6 grams (0.20 mole) of acetone, 75 grams (0.80 mole) of phenol, 22 grams (0.20 mole) of chlorotrimethyl silane, and 0.10 gram of butanethiol. The resulting mixture was stirred mechanically and heated at 55° C. under a nitrogen atmosphere for 3 hours. On completion of the reaction, the reaction mixture was cooled to room temperature and filtered. The solid product resulting was slurried up in chlorobenzene, filtered and washed twice with chlorobenzene. Purification by recrystallization from methanol and water afforded bisphenol A with a purity of 99.5 percent in a 83 percent yield.

The aforementioned prepared bisphenol A possessed identical NMR characteristics to a bisphenol A obtained from Aldrich Chemical Company.

EXAMPLE V

Preparation of 1,1-Bis(3-methyl-4-hydroxyphenyl)cyclohexane

The preparation of the above cyclohexane was accomplished by repeating the procedure of Example I with the exception that o-cresol was employed in place of phenol. In addition, the preparation was affected in a 250-milliliter 3-necked round-bottomed flask with 0.2 mole of cyclohexanone, and without 1,2-dichloroethane as a solvent. Additionally, 108 grams of o-cresol, 22 grams of chlorotrimethyl silane, and 0.1 gram of butanethiol were employed. The reaction mixture was worked up by filtering it hot after the reaction, followed by slurrying up the filter cake in methylene chloride, filtering and washing several times with methylene chloride. There was obtained the cyclohexane product in a 76 percent yield after drying in vacuo at 80° C. for 12 hours, which product had a melting point of 190° to 191° C.

NMR(Acetone-d$_6$), δ(ppm): 1.5(m, 6H); 2.15(s, 6H), 2.2(m, 4H); 6.6 to 7.1(m, 6H); 7.85(s, 2H).

EXAMPLE VI

Preparation of 2,2-Bis(p-hydroxyphenyl)pentane

A mixture of 8.6 grams of 2-pentanone, 47 grams of phenol, 11 grams of chlorotrimethyl silane, and 0.10 grams of butanethiol was stirred and heated from 30° C. to 55° C. over a period of 1 hour. After 3 hours of heating, the reaction mixture was cooled to room temperature and filtered. The filter cake was slurried up in methylene chloride, filtered, and washed again with methylene chloride. After drying in vacuo at 80° C., there resulted the above pentane product, 18 grams with a melting point of 151° to 152° C.

NMR(Acetone-d$_6$), δ(ppm): 0.85(t, 3H); 1.15(m, 2H); 1.5(s, 3H); 2.0(m, 2H); 6.6 to 7.2(AA'BB', 8H), 8.05(s, 2H).

EXAMPLE VII

Preparation of 1,1-Bis(p-hydroxyphenyl)cyclopentane

The above bisphenol was prepared by repeating the procedure of Example VI with the exception that cyclopentanone was employed in place of 2-pentanone. The cyclopentane product resulting was purified by recrystallization from a methanol and water mixture. The yield was 66 percent, and the product had a melting point of 157° to 158° C.

NMR(Acetone-d$_6$), δ(ppm): 1.65(m, 4H); 2.25(m, 4H); 6.7 to 7.2(AA'BB', 8H); 8.05(s, 1H).

EXAMPLE VIII

Preparation of 2,2-Bis(3-methyl-4-hydroxyphenyl)propane

The above propane was prepared by repeating the procedure of Example V with the exception that acetone was selected in place of cyclohexanone. The reaction mixture was worked up by distilling off the excess cresol, the byproducts, hexamethyldisiloxane and water, followed by recrystallization from chlorobenzene. The product was obtained in 82 percent yield.

The aforementioned propane product possesses identical NMR data and melting points corresponding to a propane prepared by the conventional known HCL catelized process.

EXAMPLE IX

Preparation of 3,3-Bis(3-methyl-4-hydroxyphenyl)pentane

The procedure of Example V was repeated with the exception that 3-pentane was selected in place of cyclohexanone. The above pentane product was obtained in a yield of 67 percent.

The aforementioned propane product possesses identical NMR data and melting points corresponding to the same propane prepared by the conventional known HCL catelized process.

Although the invention has been described with reference to specific preferred embodiments, it is not intended to be limited thereto, rather those skilled in the art will recognize variations and modifications may be made therein which are within the spirit of the present invention and within the scope of the following claims.

What is claimed is:

1. A process for the preparation of gem-bis(hydroxyaryl)alkanes which comprises the reaction, at a temperature of from about 30° C. to about 80° C., of a ketone, a hydroxyarene, and an alkylhalosilane.

2. A process in accordance with claim 1 wherein the silane selected is chlorotrimethyl silane.

3. A process in accordance with claim 1 wherein the silane selected is bromotrimethyl silane.

4. A process in accordance with claim 1 wherein the reaction is accomplished in the presence of a catalyst.

5. A process in accordance with claim 4 wherein there is selected from about 0.001 mole equivalents to about 0.05 mole equivalents of the catalyst.

6. A process in accordance with claim 4 wherein the catalyst is a thiol.

7. A process in accordance with claim 4 wherein the catalyst is butanethiol.

8. A process in accordance with claim 1 wherein the bisalkane is obtained in a yield of greater than 65 percent.

9. A process in accordance with claim 1 wherein the bisalkane obtained has a purity of from about 95 percent to about 99.5 percent.

10. A process in accordance with claim 1 wherein the bisalkane obtained is bisphenol (Z).

11. A process in accordance with claim 1 wherein the bisalkane obtained is 1,1-bis(3-methyl-4-hydroxyphenyl)-cyclohexane.

12. A process in accordance with claim 1 wherein the bisalkane obtained is 1,1-bis(p-hydroxyphenyl)cyclopentane.

13. A process in accordance with claim 1 wherein the reaction is accomplished in the presence of a solvent.

14. A process in accordance with claim 13 wherein the solvent is an aliphatic halogenated hydrocarbon.

15. A process in accordance with claim 14 wherein the aliphatic halogenated hydrocarbon contains from 1 to about 10 carbon atoms.

16. A process in accordance with claim 15 wherein the aliphatic halogenated hydrocarbon is 1,2-dichloroethane.

17. A process in accordance with claim 1 wherein the reaction is accomplished in the presence of an aromatic solvent.

18. A process in accordance with claim 17 wherein the solvent is toluene.

19. A process in accordance with claim 1 wherein subsequent to the reaction the product is separated, washed, and thereafter crystallized.

20. A process in accordance with claim 1 wherein the hydroxyarene selected is phenol.

21. A process in accordance with claim 1 wherein the hydroxyarene selected is selected from the group consisting of cresols, ethylphenols, halophenols, cyanophenols, nitrophenols, and naphthol.

22. A process in accordance with claim 1 wherein the ketone is selected from the group consisting of acetone, butanone, pentanone, cyclopentanone, substituted cyclopentanone, cyclohexanone and substituted cyclohexanone.

23. A process in accordance with claim 1 wherein the reaction is accomplished at a temperature of from about 30° to about 65° C.

24. A process in accordance with claim 1 wherein the reaction proceeds at a temperature of from about 50° to about 55° C.

25. A process for the preparation of gem-bis(hydroxyaryl)alkanes which comprises the reaction, at a temperature of from about 30° C. to about 80° C., of a ketone present in an amount of about 1 mole equivalent and selected from the group consisting of acetone, butanones, pentanones, cyclopentanone, substituted cyclopentanones, cyclohexanone, and substituted cyclohexanones; a hydroxyarene present in an amount of from about 2 mole equivalents to about 10 mole equivalents and selected from the group consisting of phenol, cresols, ethylphenols, halophenols, cyanophenols, nitrophenols, and naphthols; and an alkylhalosilane present in an amount of from about 0.1 mole equivalent to about 3 mole equivalents, having 1 to 3 alkyl substituents, each with from 1 to about 10 carbon atoms, and having 1 to 3 halogen substituents selected from the group consisting of fluoro, chloro, bromo, or iodo.

26. A process in accordance with claim 25 wherein the reaction proceeds in the presence of a catalyst present in an amount of from about 0.001 mole equivalents to about 0.05 mole equivalents, which catalyst is selected from the group consisting of alkyl thiols with from 1 to about 20 carbon atoms and aryl thiols having from 6 to about 24 carbon atoms.

27. A process in accordance with claim 26 wherein the reaction proceeds at a temperature of from about 50° to about 55° C.

* * * * *